United States Patent [19]
Haig

[11] Patent Number: 4,494,535
[45] Date of Patent: Jan. 22, 1985

[54] HIP NAIL

[76] Inventor: Armen C. Haig, 85 Pondfield Rd., Bronxville, N.Y. 10708

[21] Appl. No.: 277,039

[22] Filed: Jun. 24, 1981

[51] Int. Cl.³ .............................................. A61F 5/04
[52] U.S. Cl. .............................. 128/92 BA; 128/92 R
[58] Field of Search ............... 128/92 R, 92 A, 92 EB, 128/92 G, 92 C, 92 BC, 92 CA

[56] References Cited

U.S. PATENT DOCUMENTS

| | | | |
|---|---|---|---|
| 2,834,342 | 5/1958 | Yost | 128/92 EB |
| 3,255,747 | 6/1966 | Cochran et al. | 128/92 R |
| 4,095,591 | 6/1978 | Graham, Jr. et al. | 128/92 EB |
| 4,141,864 | 2/1979 | Rijke et al. | 128/92 G |
| 4,261,350 | 4/1981 | Branemark et al. | 128/92 BC |
| 4,274,163 | 6/1981 | Malcom et al. | 128/92 C |

OTHER PUBLICATIONS

Zimmer Catalog, 1978, p. B 84, Haig Nail, of Warsaw, Indiana 46580.

Primary Examiner—John D. Yasko
Assistant Examiner—C. W. Shedd
Attorney, Agent, or Firm—Sherman & Shalloway

[57] ABSTRACT

A sliding hip nail implant for fixation of a fractured hip bone is provided with ports in communication with a longitudinal cannula for the introduction of an acrylic cement to stabilize the bone and adhere the nail.

3 Claims, 2 Drawing Figures

HIP NAIL

BACKGROUND

Fixation of fractured hip bones by preparation of the bone and insertion of implants in the form of nails or screws has received the attention of many over the years. It is a common surgical procedure.

A wide variety of implants is now available to the surgeon. Many hip fractures occur in older people wherein the bone structure may be weakened or osteoporotic, with the result that the implant is not securely held. Exemplary of the present state of the art is my "Haig Sliding Nail" sold by Zimmer USA, Inc. This implant comprises an elongate nail member and a plate for attachment to the bone by screws. The upper end of the plate has a bore for receiving the shank of the nail and allows some lateral sliding of the nail with respect to the plate. The distal or head end of the nail is triflanged. The nail is cannulated with a longitudinal axial passageway to accept a guide pin.

BRIEF DESCRIPTION OF INVENTION

The present invention adds to the Haig Sliding Nail several ports in the flutes between flanges at the head of the nail. The ports communicate with the cannula and together provide a conduit for the injection of a hardenable liquid polymer after placement of the nail. The polymer serves to reinforce the bone structure in the vicinity of the nail and also serves as a gap filling adhesive to bond and fix the nail to the bone to improve holding power and provide earlier weight bearing.

DESCRIPTION OF A PREFERRED EMBODIMENT

Figure 1:
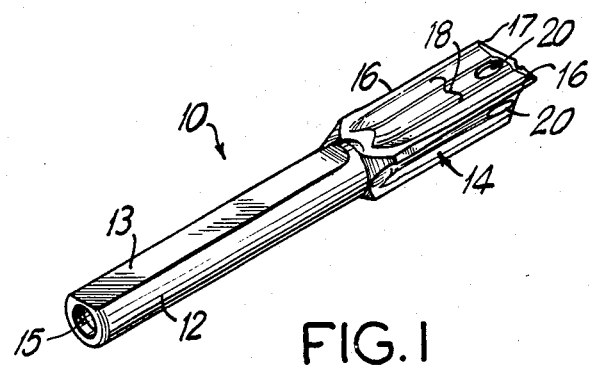
FIG. 1 is a perspective view of the nail of the present invention.

Referring now to FIG. 1, the nail 10 comprises a shank 12 and head 14 at the distal or inboard end. The head 14 comprises three flanges 16 separated by flute areas 18. The leading end 17 of each flange is sharpened to aid in impact placement of the nail in the bone. The shank 12 is provided with a flat 13 which cooperates with a key or boss in the bore of the plate to prevent substantial rotation while allowing lateral sliding motion. The entire length of the nail is cannulated by a small diameter bore 15 which may be threaded at the proximal or outboard end. The cannula accepts a guide wire which may be used in the bone boring operation and for guiding the nail as it is impact driven into position. Threads in the proximal end permit attachment of tooling such as inserters, impactors, and extractors. They also may be used to attach a syringe of polymeric material to be described below. In the fluted region 18 of the distal head are located one or more ports 20 in communication with the cannula 15.

Figure 2:
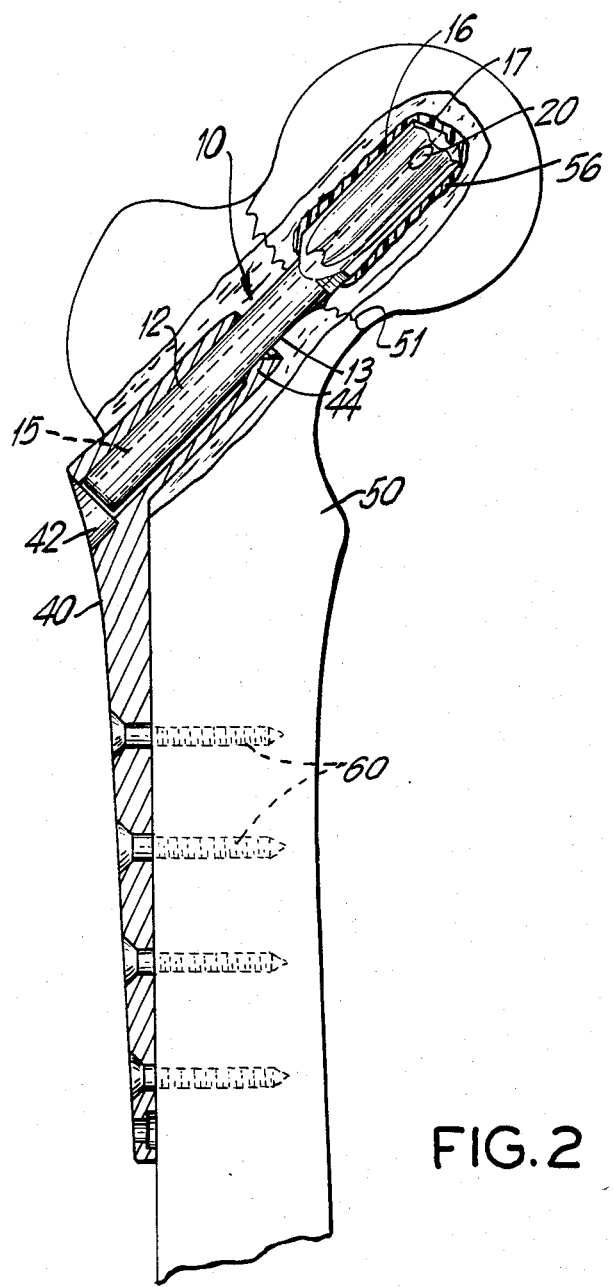
FIG. 2 is a view in section of the nail and plate in position in a fractured bone.

FIG. 2 shows the nail 10 in place in a hip bone 50 having a fracture 51 which has been reduced and has been stabilized by the nail 10. The shank 12 of the nail is accepted in a bore 42 of a plate 40 affixed to the shaft of the bone by screws 60. A small boss or key 44 in the bore 42 of the plate bears against the flat 13 of the nail shank 12 to prevent substantial relative rotation of the nail and plate. Cannula 15 is in communication with ports 20 at the distal or head end of the nail. Polymer 56, ejected from port 20 by the below described technique permeates the surrounding bone to stabilize it and to adhere to the nail 10.

The operative procedure for placement of the nail of the present invention is conventional until after the nail is in place. Since that procedure is conventional, it will not be detailed here.

Use of the nail of the present invention is indicated under the following conditions; extreme osteoporosis, poor bone stock, high (valgus) nailing angle, an older patient, or pathological fracture. The primary departure from the regular technique and the most essential technical consideration is the necessity to avoid any penetration into the hip joint. The reasons for this will be obvious. The nail must be enclosed completely within the femoral head segment before introduction of low viscosity cement is considered.

The cement package is kept cold in the refrigerator at the start of the procedure to insure against any early setting of the cement. This also insures maximum length of the liquid phase of the cement necessary for its injection through the guide wire cannula 15.

The nail is introduced into the femoral head in the usual way and the plate is applied. The nail can be retracted approximately 2 to 3 millimeters prior to injection of the cement. An angiocath 14 ga. (cut down) catheter is then passed through the cannula and placed on suction to clear out the cannula.

An adaptor is then screwed into the nail. The cement is mixed, and poured into a 20 cc syringe. The opening of the syringe is kept closed with a finger tip as the cement is poured into the syringe. The cement is poured to the top of the syringe before applying the plunger to avoid any airlock in the cement mass. The plunger is driven into the syringe with the syringe held over a bowl to assure maximum pressure and a uniform cement mass on final delivery. The first 5 or 6 ml of cement removed from the syringe can be discarded. The syringe is then applied to the adaptor already in the base of the nail. Approximately 2½ to 3 ml of cement is injected through the cannula 15. The injection can be monitored on a video screen X-ray monitor. Usually a blush on the tip of the nail can be seen as the injection proceeds. In an extremely osteoporotic head, up to 5 ml may be required, but usually not more. Note that the cement is delivered through the side ports and the tip of the nail. None will be seen at the fracture site.

When cement delivery is complete, remove the syringe. A driver is then applied to the base of the nail and the nail tapped gently to its original seating position. This step can be eliminated if cement penetration and the seating of the nail in its original position are satisfactory. Driving the nail into the cement further insures good contact between the nail and the cement mass. The threads in the base of the nail are occupied by the adaptor to avoid cement in the cannula threads should later extraction be required. The nail should not be twisted during the cement setting phase to insure good purchase of the nail and the cement in the head of the femur.

The cement will cure without further attention of the operating surgeon. Upon cure of the cement (as tested by the remainder of the cement in the syringe) the adaptor is removed from the base of the nail. The rest of the closure is routine.

The acrylic cement preferred is that sold by Zimmer USA, Inc. under the trademark L.V.C. This is a low viscosity two part acrylic liquid cement which polymerizes after mixing, but provides adequate working time and adequately low viscosity to permit syringe injection. The hardened cement 56 adheres to and embeds the nail 10 in the bone mass and permeates and stabilizes the bone. Early weight bearing is characteristic and is due to the cushioning effect of the acrylic cement.

I claim:

1. In a hip fixation nail for treating a fractured hip bone comprising a shank having a head portion at the distal end thereof, the head portion comprising a plurality of flanges separated by fluted areas, the entire length of the nail being cannulated by a bore; an elongated plate, attachable by means of fasteners to said bone, having bore means adjacent one end thereof for cooperatively receiving said shank; the improvement wherein a plurality of ports are located in the fluted areas in communication with the bore adjacent the distal end to allow deposition of a hardenable liquid polymeric material in the area surrounding the head portion but not at the fracture site in the hip bone to form a tighter bond between the nail and the fractured hip bone.

2. A method for treating a fractured hip bone comprising inserting into the fractured hip bone the head portion of a hip fixation nail comprising a shank having a head portion at the distal end thereof, the head portion comprising a plurality of flanges separated by fluted areas, the entire length of the nail being cannulated by a bore, a plurality of ports being located in the fluted areas in communication with the bore; injecting through the bore in the nail a hardenable liquid polymeric material into the region surrounding the head portion but not the fracture site; monitoring the cement injection procedure by means of fluoroscopic visual control; and permitting the polymeric material to harden.

3. The method of claim 2 wherein the polymeric material is an acrylic cement.

* * * * *